US009517775B2

United States Patent
Gensler et al.

(10) Patent No.: US 9,517,775 B2
(45) Date of Patent: Dec. 13, 2016

(54) METHOD, DEVICE, AND COMPUTER PROGRAM PRODUCT FOR OPERATING A MOTOR VEHICLE

(71) Applicant: Bayerische Motoren Werke Aktiengesellschaft, Munich (DE)

(72) Inventors: Frank Gensler, Neubiberg (DE); Ulrich Langenkamp, Neubiberg (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 14/598,682

(22) Filed: Jan. 16, 2015

(65) Prior Publication Data

US 2015/0203122 A1   Jul. 23, 2015

(30) Foreign Application Priority Data

Jan. 17, 2014   (DE) .................. 10 2014 200 783

(51) Int. Cl.
   *B60W 40/08*   (2012.01)
   *A61B 5/0205*  (2006.01)
   (Continued)

(52) U.S. Cl.
   CPC ............ *B60W 40/08* (2013.01); *A61B 5/0205* (2013.01); *A61B 5/1102* (2013.01); *A61B 5/1112* (2013.01);
   (Continued)

(58) Field of Classification Search
   CPC ........ A61B 5/18; A61B 5/0205; B60W 40/08; G01B 11/00
   See application file for complete search history.

(56) References Cited

U.S. PATENT DOCUMENTS

2008/0069403 A1   3/2008  Breed
2012/0150387 A1*  6/2012  Watson ............... A61B 5/0077
                                                          701/36

(Continued)

FOREIGN PATENT DOCUMENTS

DE   10 2004 035 896 A1   3/2006
DE   10 2012 201 071 A1   7/2012
DE   10 2011 110 486 A1   2/2013

OTHER PUBLICATIONS

German Search Report dated Jan. 19, 2015 with partial English translation (12 pages).

*Primary Examiner* — Michael D Lang
(74) *Attorney, Agent, or Firm* — Crowell & Moring LLP

(57) ABSTRACT

In order to operate a motor vehicle, a position sensor and a radiation source as well as at least one vital sensor having a detector are provided. The position sensor delivers a measurement signal having information regarding a predetermined area of the vehicle interior of the motor vehicle. The radiation source emits a predetermined radiation after activation. The vital sensor detects a reflected portion of the radiation that is emitted by the radiation source. The measurement signal of the vital sensor is representative of at least one vital parameter of a given vehicle occupant. As a function of the measurement signal of the position sensor, a position is determined of at least one predetermined reference body part of the vehicle occupant in question. The orientation of the radiation source is controlled as a function of the detected position of the predetermined reference body part of the vehicle occupant in question.

19 Claims, 2 Drawing Sheets

(51) Int. Cl.
| | |
|---|---|
| *A61B 5/11* | (2006.01) |
| *A61B 5/117* | (2016.01) |
| *A61B 5/18* | (2006.01) |
| *A61B 5/00* | (2006.01) |
| *A61B 8/00* | (2006.01) |
| *G01B 11/00* | (2006.01) |
| *G06K 9/00* | (2006.01) |
| *A61B 5/1455* | (2006.01) |
| *G06K 9/20* | (2006.01) |

(52) U.S. Cl.
CPC ............ *A61B 5/1128* (2013.01); *A61B 5/1176* (2013.01); *A61B 5/18* (2013.01); *A61B 5/6893* (2013.01); *A61B 8/00* (2013.01); *G01B 11/00* (2013.01); *G06K 9/00362* (2013.01); *G06K 9/00845* (2013.01); *A61B 5/14551* (2013.01); *G06K 9/2027* (2013.01)

(56) References Cited

U.S. PATENT DOCUMENTS

| | | |
|---|---|---|
| 2012/0188355 A1 | 7/2012 | Omi et al. |
| 2014/0221781 A1 | 8/2014 | Schrauf et al. |

\* cited by examiner

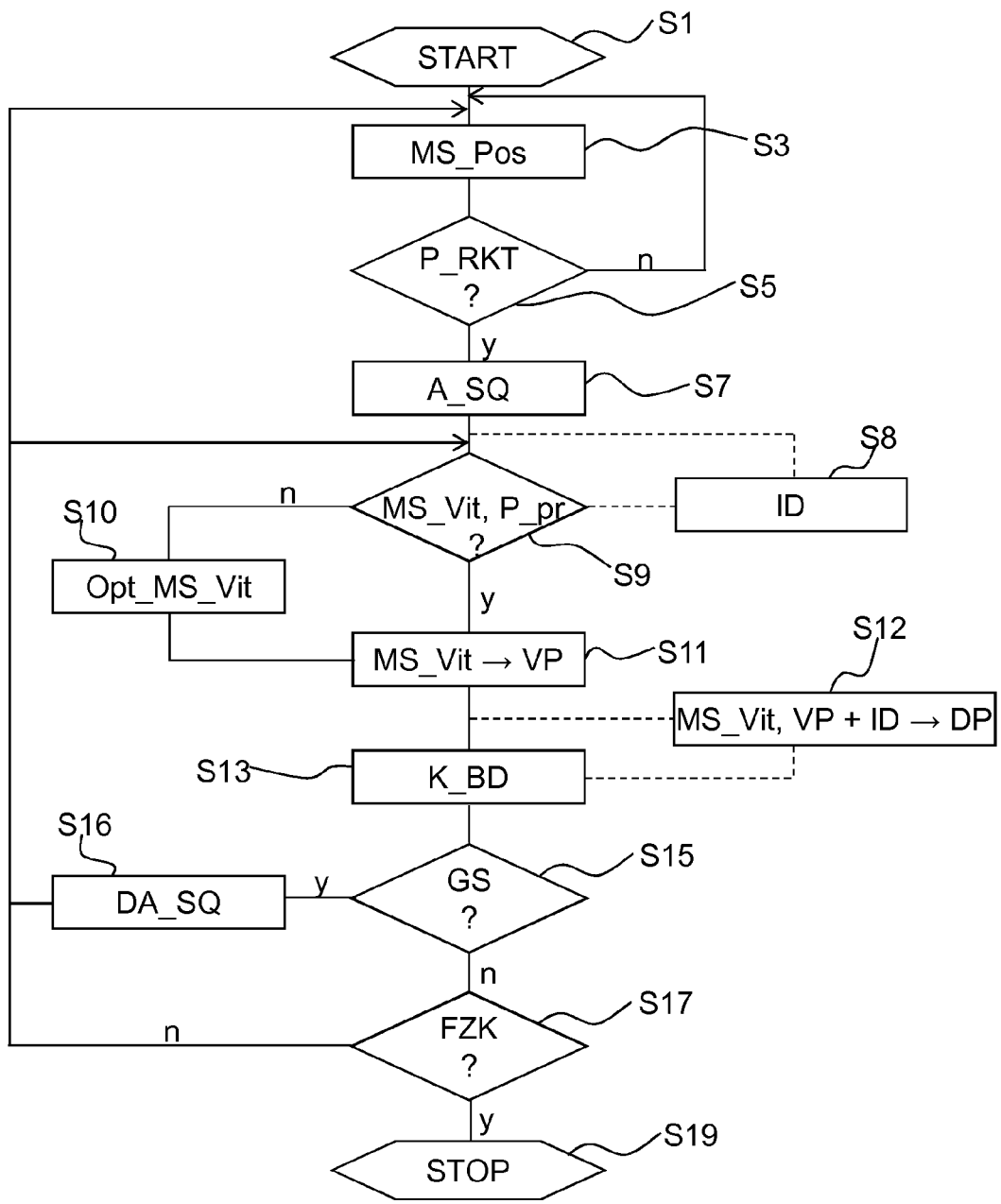

METHOD, DEVICE, AND COMPUTER PROGRAM PRODUCT FOR OPERATING A MOTOR VEHICLE

CROSS REFERENCE TO RELATED APPLICATION

This application claims priority under 35 U.S.C. §119 from German Application No. 10 2014 200 783.6, filed Jan. 17, 2014, the entire disclosure of which is herein expressly incorporated by reference.

BACKGROUND AND SUMMARY OF THE INVENTION

The invention relates to a method, a device, and a computer program product for operating a motor vehicle in which a radiation source is controlled dependent upon a position sensor.

Motor vehicles are being increasingly equipped with cameras or sensors. These cameras or sensors may be used, for example, for monitoring the health status of the vehicle occupant. Monitoring the health status of the vehicle occupant can contribute to increasing traffic safety.

The object of the invention is to create a method and corresponding device that contributes to the health status of the vehicle occupant being reliably detectable.

This and other objects are achieved by a method for operating a motor vehicle, with which a position sensor is assigned whose measurement signal includes spatial information regarding a predetermined area of a vehicle interior of the motor vehicle. At least one radiation source is associated that emits a predetermined radiation. At least one vital sensor having a detector is associated that detects a portion of the radiation emitted by the radiation source striking it and whose measurement signal is representative of at least one vital parameter of a given vehicle occupant. As a function of the measurement signal of the position sensor, a position of at least one predetermined reference body part of the vehicle occupant in question is determined, and as a function of the detected position of the predetermined reference body part of the vehicle occupant in question, an orientation of the radiation source is controlled.

According to a first aspect of the invention, the invention is characterized by a method and corresponding device for the operation of a motor vehicle. According to this first aspect, a position sensor is assigned to the motor vehicle whose measurement signal captures spatial information regarding a predetermined area of a vehicle interior of the motor vehicle. Moreover, at least one radiation source is assigned to the motor vehicle that emits a predetermined radiation. Additionally, at least one vital sensor having a detector is disposed in the motor vehicle that detects the portion of the radiation emitted by the radiation source striking it. As a function of a raw measurement signal of the detector of the vital sensor, a measurement signal of the vital sensor may be generated. The measurement signal of the vital sensor is representative of at least one vital parameter of a given vehicle occupant. As a function of the measurement signal of the position sensor, a position of at least one predetermined reference body part of the vehicle occupant in question is established. As a function of the established position of the predetermined reference body part of the vehicle occupant in question, an orientation of the radiation source is controlled.

In this manner, the radiation source in the motor vehicle may be controlled in a simple and reliable fashion. Due to the position sensor, the orientation of the radiation source may be adapted to a movement of the vehicle occupant in question or at least to a movement of the predetermined reference body part. Thus, it is possible to guarantee that, even when the vehicle occupant in question moves, a reflected portion of the radiation emitted by the radiation source will strike the vital sensor. Here, the predetermined reference body part of the vehicle occupant in question is used as a reference to establish the direction in which the radiation from the radiation source should be directed in order to allow the determination of the at least one vital parameter. In addition, by virtue of the movement-adapted orientation of the radiation source, it is possible to contribute to the safety of the vehicle occupant in question.

According to one embodiment of the first aspect, the at least one vital parameter of the vehicle occupant in question is detected as a function of the measurement signal of the vital sensor.

In this context, the radiation source is particularly directed at an area of skin of the vehicle occupant in question, for example, at his or her neck or in the facial area. The portion of the predetermined radiation reflected on the area of skin can provide information regarding one or more vital parameters of the vehicle occupant in question such that, in this manner, one or more vital parameters may be ascertained in a contact-free fashion without limiting the movement of the vehicle occupant in question. In this manner, it is not necessary for sensors to be directly attached to the vehicle occupant in question, which is perceived as uncomfortable by said occupant. Moreover, the clothing of the vehicle occupant in question has no influence because, as a rule, at least the facial area of the vehicle occupant in question is not covered by clothing.

According to an additional embodiment of the first aspect, the at least one vital parameter of the vehicle occupant in question is detected as a function of the measurement signal of the vital sensor on the basis of vibrocardiography.

Vibrocardiography is a method in which radiation from a radiation source, for example, laser light, is directed onto a surface of an object to be examined and a reflected portion of the laser light is analyzed. Based on the surface structure of the object, the laser light is reflected in such a way that an interference structure may be observed at a corresponding distance from the object that contains information regarding the composition of the surface and the movement of the object. In this context, vibrocardiography may be used for the detection of vital parameters in that the radiation from the radiation source is directed onto an area of skin of the occupant in question and the reflected portion of this radiation is detected by means of the vital sensor and the measurement signal of the vital sensor is subsequently processed. For example, a laser used as a radiation source may be directed onto the region of the carotid artery of the vehicle occupant in question, such that, due to the pulsing carotid artery, a periodic movement of the reflected interference structure may be observed. Thus, for example, a pulse or even a pulse type of the vehicle occupant in question may be detected.

According to another embodiment of the first aspect, the at least one vital parameter of the vehicle occupant in question is determined as a function of the measurement signal of the vital sensor on the basis of photo oximetry. In this context, photo oximetry describes a method in which radiation from a radiation source, for example, laser light, is directed onto an object to be investigated and the reflected and/or transmitted portion of the laser light is analyzed. For example, laser light reflected against an area of skin of the vehicle occupant in question may be analyzed with regard to its intensity. In this manner, for example, blood oxygen content and/or blood sugar levels may be ascertained as a vital parameter of the vehicle occupant in question in a contact-free manner. Blood oxygen content as well as blood sugar levels of the vehicle occupant in question have an effect on the coloration of the blood, for which reason, for example, oxygen-richer blood appears brighter than low-oxygen blood. The different coloration of the blood within the area of skin of the vehicle occupant in question leads to a different intensity of the reflected laser light such that, in this manner, the required vital parameters may be ascertained by the analysis of the reflected laser light.

According to an additional embodiment of the first aspect, as a function of the detected position of the reference body part of the vehicle occupant in question and the measurement signal of the vital sensor, the radiation source is controlled in the sense of its orientation toward at least one prespecified preferred position of the vehicle occupant in question.

In this manner, a high degree of correlation of the measurement signal of the vital sensor to the respective vital parameter becomes possible. A preferred position in this context may be a carotid artery or a temple of the vehicle occupant in question.

Another option lies in activating more than one predetermined preferred position of the vehicle occupant in question as a function of the measurement signal of the vital sensor. For example, in the case of one vehicle occupant, a good correlation of the measurement signal of the vital sensor to the respective vital parameter may be obtained by orienting the radiation source toward the carotid artery and, in the case of another vehicle occupant, by orienting the radiation source toward the region of the temple.

Moreover, one of the preferred positions, such as an area of skin on the neck of the vehicle occupant in question, may be covered by a piece of clothing, for example, a scarf. For this reason, another preferred position, such as the region of the temple, may be suitable for ascertaining the at least one vital parameter of the vehicle occupant in question.

The preferred position in which, for a given vehicle occupant, the highest correlation is present between the measurement signal of the vital sensor and the respective vital parameter to be ascertained may be designated as the optimal preferred position on that specific vehicle occupant.

Alternatively or additionally, it may be advantageous for the orientation of the radiation source to be optimized with respect to the greatest possible correlation between the measurement signal of the vital sensor and the respective vital parameter to be ascertained. In this context, the radiation from the radiation source is initially oriented toward a prespecified preferred position on the vehicle occupant in question and the radiation from the radiation source is varied in the sense of an orientation in a prespecified area around the prespecified preferred position. By evaluating where the respective measurement signal of the vital sensor has the greatest correlation to the respective vital parameter, an adapted preferred position may be ascertained accordingly.

According to an additional embodiment of the first aspect, a radiation intensity of the radiation source is controlled as a function of the measurement signal of the vital sensor.

In this manner, it becomes possible for an intensity of the reflected portion of the radiation to reach a prespecified second threshold value, thus allowing the reception of a measurement signal of the vital sensor. For example, a prespecified signal-to-noise ratio may be attained in this manner such that the detection of at least one vital parameter of the vehicle occupant in question becomes possible.

According to an additional embodiment of the first aspect, the radiation source is activated or deactivated as a function of the measurement signal of the position sensor. In this manner, the safety of the vehicle occupant in question is ensured, inter alia, in that the radiation source is not activated until the position of the vehicle occupant in question and/or of the respective predetermined reference body part has been ascertained.

In addition, this embodiment includes the contact-free measurement of the at least one vital parameter of the vehicle occupant in question, for example, by use of a plurality of radiation sources disposed in the motor vehicle. Thus, for example, one radiation source may be positioned in a headrest of the vehicle occupant in question and oriented toward an area of skin on the neck of the vehicle occupant in question. Another radiation source may be disposed in the instrument panel of the motor vehicle and be directed toward an area of skin in the region of one of the temples of the vehicle occupant in question.

Moreover, by the activation or deactivation of the radiation source, the measurement and detection of the at least one vital parameter of the vehicle occupant in question may occur within a certain time interval and need not be conducted continuously for the duration of the driving cycle.

According to another embodiment of the first aspect, a characteristic value is determined for a movement dynamic as a function of the measurement signal of the position sensor. Moreover, as a function of the characteristic value for the movement dynamic, the radiation source is activated or deactivated.

For example, depending on the situation, a rapid movement of the vehicle occupant in question may occur that the radiation source may not necessarily be able to follow with regard to its orientation. If, in this context, a characteristic value is determined for the movement dynamics that exceeds a predetermined third threshold value, the radiation source may be deactivated. In this manner, the safety of the vehicle occupant in question is guaranteed even in the case of sudden movements.

According to another embodiment of the first aspect, the position sensor comprises a camera. In this context, the camera may be embodied as an individual camera or as a stereo camera and thus provide spatial information for a predetermined area of the vehicle interior of the motor vehicle. Cameras are already frequently disposed in motor vehicles for other purposes such that, for example, a pre-existing resource may be used in this situation.

According to another embodiment of the first aspect, the position sensor comprises an ultrasonic sensor. This is another option for capturing spatial information in a predetermined area of the vehicle interior of the motor vehicle.

According to another embodiment of the first aspect, the radiation source comprises a laser. Due to its radiation properties, the laser represents a preferred radiation source that emits coherent light with a high degree of brilliance. For this reason, laser light may be directed in a controlled fashion at an area of skin of the vehicle occupant in question. By analyzing the portion of the laser radiation reflected on the area of skin, a vital parameter of the vehicle occupant in question may be determined using, for example, vibrocardiography or photo oximetry.

According to another embodiment of the first aspect, a person sensor is assigned to the motor vehicle whose measurement signal is representative of a personal identifying characteristic of the vehicle occupant in question. An identification is conducted as a function of the measurement signal of the person sensor, thus providing an identified vehicle occupant.

In this manner, the measurement of the vital parameter or parameters may be associated with the identified vehicle occupant, thus allowing, for example, a person-specific measurement of the at least one vital parameter.

Moreover, the identification of the vehicle occupant in question allows one or more predetermined preferred positions to be associated with the identified vehicle occupant in question. Thus, for example, a data memory may be used to store which preferred position of the identified vehicle occupant in question was found to be the optimal preferred position for determining the vital parameter or parameters during the previous driving cycle such that, in a subsequent driving cycle, the optimal preferred position for the identified vehicle occupant in question may be activated by the radiation source.

Moreover, the respectively adapted preferred position may be stored in relation to the identified vehicle occupant in question. Thus, when the vehicle occupant in question is identified again during a subsequent driving cycle, information is available regarding the optimal preferred position of the identified vehicle occupant and regarding a person-specific optimized orientation of the radiation source in the region of the optimal preferred position.

According to another embodiment of the first aspect, the position sensor is additionally used as a person sensor. In this manner, a pre-existing sensor is used for an additional purpose and additional sensors are not necessarily required.

According to another embodiment of the first aspect, a respective trend of the measurement signal of the vital sensor is associated with the identified vehicle occupant in question. Thus, it is possible for the measurement signal of the vital sensor to be directly associated with an identified vehicle occupant without any additional analysis. Further analysis of the measurement signal may occur, for example, outside of the motor vehicle and/or at a later time.

According to a second aspect, one system comprises the device for operating a motor vehicle, the position sensor, the radiation source, and the vital sensor with the detector.

According to a third aspect, the invention is characterized by a computer program product comprising executable program code, with the program code performing the method for operating a motor vehicle according to the first aspect upon its execution by a data processing unit.

Other objects, advantages and novel features of the present invention will become apparent from the following detailed description of one or more preferred embodiments when considered in conjunction with the accompanying drawings.

BRIEF DESCRIPTION OF THE DRAWINGS

FIG. 2 is a flowchart of a program that is executed in the device.

DETAILED DESCRIPTION OF THE DRAWINGS

Figure 1:
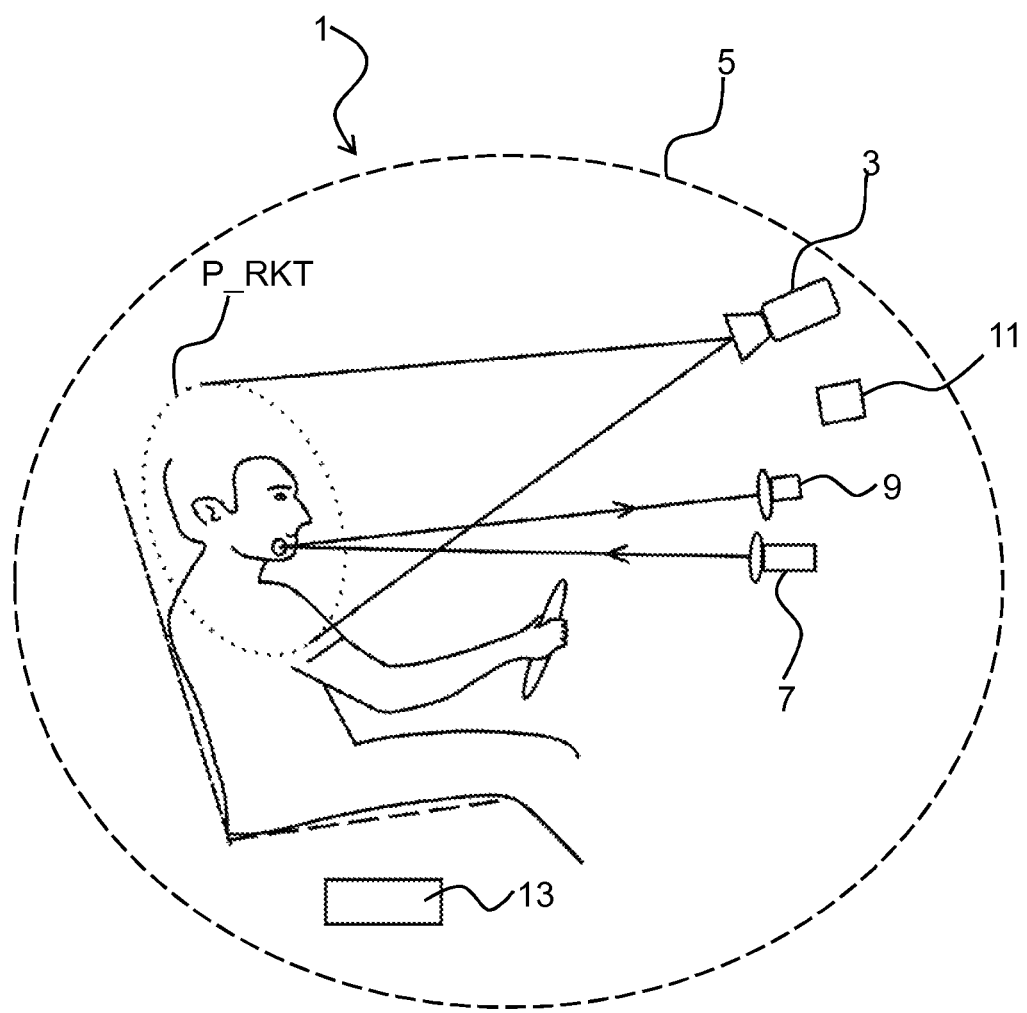
FIG. 1 is a schematic diagram of a motor vehicle having a device for operating a motor vehicle.

Elements having the same structure or function have been assigned the same reference characters in both figures.

A position sensor 3, a vital sensor 9 having a detector, and a radiation source 7 are associated with a motor vehicle (FIG. 1). The radiation source 7 emits a predetermined radiation upon activation. A measurement signal MS_Pos of the position sensor 3 includes spatial information regarding a predetermined area of the vehicle interior 5 of the motor vehicle 1. A measurement signal MS_Vit of the vital sensor 9 includes a reflected portion of the radiation that was emitted by the radiation source 7 and is representative of at least one vital parameter VP of a respective vehicle occupant.

In addition, a person sensor 11 and a control unit 13 are disposed in the motor vehicle 1.

The control unit 13 may include, for example, a data and program memory as well as a processing unit. It may be designated as a device for operating a motor vehicle or even as an on-board computer. The control unit 13 is connected via a signal to the position sensor 3, the vital sensor 9, and the radiation source 7.

The person sensor 11 provides a measurement signal MS_Per that is representative of a personally identifying characteristic of the vehicle occupant in question, such that said occupant is identified as a function of the measurement signal MS_Per.

If the vehicle occupant is the driver of the motor vehicle 1, the position sensor 3 may be disposed, for example, in a front area of the vehicle interior 5 such as, for example, in a corner in the region of the windshield of the motor vehicle 1. The radiation source 7, the vital sensor 9, and the person sensor 11 may then be disposed, for example, in the instrument panel of the motor vehicle 1. If the vehicle occupant in question is sitting on a backseat of the motor vehicle 1, the position sensor 3, the radiation source 7, the vital sensor 9, and the person sensor 11 may, for example, be integrated into a headrest of the occupant in front of said occupant or in the region of an arm rest of the motor vehicle 1.

A flowchart (FIG. 2) shows a program that is executed in the control unit 13 of the motor vehicle 1.

In a step S1, the program is started in which, for example, variables are initialized. The start of the program may occur, for example, around the same time as the engine of the motor vehicle 1 is started.

In a step S3, the measurement signal MS_Pos of the position sensor 3 is read and temporarily stored.

In a step S5, an analysis is conducted as a function of the measurement signal MS_Pos of the position sensor 3 as to whether a position P_RKT of at least one predetermined reference body part of the vehicle occupant in question can be determined. If the position P_RKT of at least one predetermined reference body part can be determined, then the program is continued in a step S7. Otherwise, the program can proceed from step S3 again.

In the step S7, the radiation source is activated and a predetermined radiation is thus emitted. Here, the position P_RKT of the predetermined reference body part serves as a reference point for the orientation of the radiation source 7. The program may be subsequently continued in an optional step S8 or in a step S9.

In the optional step S8, the identity of the vehicle occupant in question may be determined with the aid of the person sensor 11. In this context, for example, it is possible for an actual value of the personal identifying characteristic to be determined as a function of the measuring signal MS_Per. By comparing the actual value of the personal identifying characteristic to a predetermined target value which is stored, for example, in the memory of the control unit 13, a degree of correlation may be determined. In this context, the degree of correlation may provide a percentage correlation of the actual value with the target value such that the identification of the vehicle occupant in question may be categorized as successful or unsuccessful in relation to a first threshold value provided in the program. If the identification of the vehicle occupant in question has been successfully conducted, the identified vehicle occupant in question is assigned a personal identifier ID that represents the identified vehicle occupant in question.

In a subsequent step S9, the measurement signal MS_Vit of the vital sensor 9 is read and temporarily stored. In this context, the radiation from the radiation source 7 is directed toward a predetermined preferred position P_pr on the vehicle occupant in question. This position may be, for example, a section of skin on the neck or the region of a temple of the vehicle occupant in question.

In addition, a determination is made in the step S9 as to whether the measurement signal MS_Vit of the vital sensor 9 is such that the determination of at least one vital parameter VP of the vehicle occupant in question is possible. This may be verified, for example, by whether or not the measurement signal MS_Vit of the vital sensor 9 exceeds a predetermined second threshold value. This may be verified, for example, by a predetermined signal-to-noise ratio. In this case, a value of an amplitude of the detected measurement signal MS_Vit of the vital sensor 9 is placed in a ratio to a value of a constantly present background signal. If the value of this ratio exceeds the predetermined second threshold value, then the program is continued in a step S11. Otherwise, the program is continued in a step S10.

In the step S10, the radiation source 7 is varied with regard to its orientation and/or radiation intensity in order to thus achieve the predetermined second threshold value. This guarantees that at least one vital parameter VP of the vehicle occupant in question may be determined from the detected measurement signal MS_Vit of the vital sensor 9.

For example, the orientation of the radiation source 7 may be varied as a function of the measurement signal MS_Vit of the vital sensor 9 relative to a predetermined preferred position P_pr in such a way that the measurement signal MS_Vit of the vital sensor 9 is optimized with regard to its amplitude.

Another option lies in multiple preferred positions P_pr being predetermined such that an optimal preferred position P_pr_opt is determined. In this context, the optimal preferred position P_pr_opt on the vehicle occupant in question is the preferred position P_pr in which the orientation of the radiation source 7 is optimized with regard to an optimal correlation of the measurement signal MS_Vit of the vital sensor 9 and the respective vital parameter VP of the vehicle occupant in question to be determined. For example, this may be the preferred position P_pr in which the measurement signal MS_Vit of the vital sensor 9 has the greatest value for its amplitude or, in reference to the above-mentioned example, the greatest signal-to-noise ratio is present.

Alternately or additionally, the signal-to-noise ratio may be varied by adapting the radiation intensity of the radiation emitted by the radiation source 7. If, for example, the radiation source 7 is directed at the preferred position P_pr, the radiation intensity may be adapted until the predetermined second threshold value of the signal-to-noise ratio of the measurement signal MS_Vit of the vital sensor 9 has been reached.

In addition, the need for more than one predetermined preferred position P_pr may lie in the fact that a preferred position such as, for example, an area of skin on the neck of the vehicle occupant in question, is covered by a piece of clothing, for example, a scarf. For this reason, another preferred position P_pr such as, for example, an area of skin in the region of the temple of the vehicle occupant in question, may be suitable for the detection of at least one vital parameter VP.

If an identified vehicle occupant was detected in the optional step S8, it is possible, for example, using the radiation source 7, for the optimal preferred position P_pr_opt of the identified vehicle occupant in question to be activated that may have already shown itself to be suitable for the identified vehicle occupant in question during a previous driving cycle FZK. Thus, for example, the carotid artery may be the optimal preferred position P_pr_opt for the duration of the method for one identified vehicle occupant and, for another identified vehicle occupant, the region of the temple. This person-related information may be stored, for example, in the memory of the control unit 13.

In another step S11, one or more vital parameters VP of the vehicle occupant in question are determined as a function of the measurement signal MS_Vit of the vital sensor 9.

In an optional step S12, based on the personal identification ID determined in the optional step S8, the measurement signal MS_Vit of the vital sensor 9 and/or the vital parameter or parameters VP determined in the step S11 of the identified vehicle occupant in question are combined into a data packet DP. The data packet DP is associated with the identified vehicle occupant in question using the personal identification ID.

In a subsequent step S13, a characteristic value K_BD for a movement dynamic of the vehicle occupant in question is determined that is representative of a movement of the vehicle occupant in question. The characteristic value K_BD may be determined, for example, inside the control unit 13 by the analysis of the measurement signal MS_Pos of the position sensor 3, which monitors the position and the movement of the vehicle occupant in question.

In a step S15, it is determined whether the characteristic value K_BD determined for the movement dynamic exceeds a predetermined third threshold value, indicating the presence of a dangerous situation GS. This may be the case, for example, when the orientation of the radiation source 7 cannot be adapted quickly enough to a movement of the vehicle occupant in question. If the characteristic value K_BD is greater than the predetermined third threshold value, a dangerous situation GS is present and the program is continued in a step S16. If the characteristic value K_BD is less than the predetermined third threshold value, no dangerous situation GS is present and the program is continued in a step S17.

In the step S16, the radiation source 7 is deactivated for safety reasons in order to prevent the radiation source 7 from endangering the vehicle occupant in question in the case of a sudden movement by the vehicle occupant in question. For example, if a laser is used as the radiation source 7, this can prevent the laser light from propagating in the direction of an area of the eyes of the vehicle occupant in question, thus blinding the vehicle occupant or endangering his or her health. Subsequently, the position sensor 3 continues to monitor the movement dynamic of the vehicle occupant in question and the characteristic value K_BD of the movement dynamic continues to be determined until the characteristic value K_BD falls below the predetermined third threshold value. The program is then continued in step S3 or S7.

In step S17 it is determined whether or not the current driving cycle FZK has ended. If, based on step S15, no dangerous situation GS has been detected and the current driving cycle FZK is not considered to have ended, the program is continued in step S9. The recording and temporary storage of the measurement signal MS_Vit of the vital sensor 9 is correspondingly continued at the activated preferred position P_pr. Otherwise, the current driving cycle FZK is considered to have ended and the program is continued in a step S19.

In step S19, the program is ended.

LIST OF REFERENCE CHARACTERS

1 Motor vehicle
3 Position sensor
5 Vehicle interior
7 Radiation source
9 Vital sensor
11 Person sensor
13 Control unit
MS_Pos Measurement signal, position sensor
MS_Vit Measurement signal, vital sensor
MS_Per Measurement signal, person sensor
P_RKT Position, reference body part
P_pr Preferred position
P_pr_opt Optimal preferred position
K_BD Characteristic value, movement dynamic
A_SQ Activation, radiation source
DA_SQ Deactivation, radiation source
DP Data packet
VP Vital parameter
K_BD Characteristic value, movement dynamic
FZK Driving cycle
GS Dangerous situation
Opt_MS_Vit Optimization, measurement signal, vital sensor FIG. 1

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of operating a motor vehicle, the method comprising the acts of:
   providing, via a position sensor assigned to the motor vehicle, a measurement signal that includes spatial information concerning a predetermined area of an interior of the motor vehicle;
   emitting, via at least one radiation source assigned to the motor vehicle, a predetermined radiation;
   detecting, via at least one vital sensor assigned to the motor vehicle, and having a detector, a portion of the radiation emitted by the radiation source that strikes the vital sensor, wherein:
   a measurement signal of the vital sensor is representative of at least one vital parameter of a given vehicle occupant;
   as a function of the measurement signal of the position sensor, a position of at least one predetermined reference body part and a characteristic value for a movement dynamic that is representative of a movement of the vehicle occupant in question are determined, and analysis is performed on the characteristic value to determine whether the characteristic value for the movement dynamic exceeds a predetermined threshold value; and
   as a function of the determined position of the predetermined reference body part and the analyzed characteristic value for the movement dynamic of the vehicle occupant in question, one or more following actions occur: (i) the radiation source is deactivated and (ii) an orientation of the radiation source is controlled.

2. The method according to claim 1, wherein:
   as a function of the measurement signal of the vital sensor, the at least one vital parameter of the vehicle occupant in question is determined.

3. The method according to claim 2, wherein:
   the at least one vital parameter of the vehicle occupant in question is determined as a function of the measurement signal of the vital sensor on a basis of vibrocardiography.

4. The method according to claim 3, wherein:
   the at least one vital parameter of the vehicle occupant in question is determined as a function of the measurement signal of the vital sensor on the basis of photo oximetry.

5. The method according to claim 2, wherein:
   the at least one vital parameter of the vehicle occupant in question is determined as a function of the measurement signal of the vital sensor on the basis of photo oximetry.

6. The method according to claim 1, wherein:
   as a function of the detected position of the reference body part of the vehicle occupant in question and the measurement signal of the vital sensor, the radiation source is controlled so as to be oriented toward at least one predetermined preferred position on the vehicle occupant in question.

7. The method according to claim 1, wherein:
   as a function of the measurement signal of the vital sensor, a radiation intensity of the radiation source is controlled.

8. The method according to claim 1, wherein:
   as a function of the measurement signal of the position sensor, the radiation source is activated or deactivated.

9. The method according to claim 1, wherein:
   as a function of the analyzed characteristic value for the movement dynamic, the radiation source is activated.

10. The method according to claim 1, wherein:
    the position sensor comprises a camera.

11. The method according to claim 10, wherein:
    the radiation source comprises a laser.

12. The method according to claim 1, wherein:
    the position sensor comprises an ultrasonic sensor.

13. The method according to claim 12, wherein:
    the radiation source comprises a laser.

14. The method according to claim 1, wherein:
    the radiation source comprises a laser.

15. The method according to claim 1, further comprising the acts of:
    providing, via a person sensor assigned to the motor vehicle, a measurement signal representative of a personal identification marker of the vehicle occupant in question, and
    as a function of the measurement signal of the person sensor, performing an identification to detect an identified vehicle passenger.

16. The method according to claim 15, wherein:
    the position sensor is additionally used as the person sensor.

17. The method according to claim 16, wherein:
    a respective progression of the measurement signal of the vital sensor is associated with the identified vehicle passenger in question.

18. A motor vehicle device, comprising:
a control unit comprising memory and a processor, the processor executing a computer executable program stored in the memory to:
receive, via a position sensor assigned to the motor vehicle, a measurement signal that includes spatial information concerning a predetermined area of an interior of the motor vehicle;
cause to emit, via at least one radiation source assigned to the motor vehicle, a predetermined radiation;
detect, via at least one vital sensor assigned to the motor vehicle and having a detector, a portion of the radiation emitted by the radiation source that strikes the vital sensor, wherein:
a measurement signal of the vital sensor is representative of at least one vital parameter of a given vehicle occupant;
as a function of the measurement signal of the position sensor, a position of at least one predetermined reference body part and a characteristic value for a movement dynamic that is representative of a movement of the vehicle occupant in question are determined, and analysis is performed on the characteristic value to determine whether the characteristic value for the movement dynamic exceeds a predetermined threshold value; and
as a function of the detected position of the predetermined reference body part and the analyzed characteristic value for the movement dynamic of the vehicle occupant in question, one or more following actions occur: (i) the radiation source is deactivated and (ii) an orientation of the radiation source is controlled.

19. A motor vehicle system, comprising:
a position sensor;
a radiation source;
a vital sensor with a detector; and
a control unit comprising memory and a processor, the processor executing a computer executable program stored in the memory to:
receive, via the position sensor assigned to the motor vehicle, a measurement signal that includes spatial information concerning a predetermined area of an interior of the motor vehicle;
cause to emit, via the radiation source assigned to the motor vehicle, a predetermined radiation;
detect, via the vital sensor assigned to the motor vehicle, a portion of the radiation emitted by the radiation source that strikes the vital sensor, wherein:
a measurement signal of the vital sensor is representative of at least one vital parameter of a given vehicle occupant;
as a function of the measurement signal of the position sensor, a position of at least one predetermined reference body part and a characteristic value for a movement dynamic that is representative of a movement of the vehicle occupant in question are determined, and analysis is performed on the characteristic value to determine whether the characteristic value for the movement dynamic exceeds a predetermined threshold value; and
as a function of the detected position of the predetermined reference body part and the analyzed characteristic value for the movement dynamic of the vehicle occupant in question, one or more following actions occur: (i) the radiation source is deactivated and (ii) an orientation of the radiation source is controlled.

* * * * *